United States Patent
Blilie et al.

(10) Patent No.: US 10,828,496 B2
(45) Date of Patent: Nov. 10, 2020

(54) CORE-CLIP PG-LEAD SPRING ELECTRICAL CONTACT

(71) Applicant: Cardiac Pacemakers, Inc., St. Paul, MN (US)

(72) Inventors: James Blilie, Shoreview, MN (US); Arthur J. Foster, Blaine, MN (US); Jack Gordon, Minneapolis, MN (US); Bruce K. Gilbertson, Coon Rapids, MN (US); Steven A. Kubow, Hugo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/460,627

(22) Filed: Jul. 2, 2019

(65) Prior Publication Data

US 2020/0016413 A1  Jan. 16, 2020

Related U.S. Application Data

(60) Provisional application No. 62/697,203, filed on Jul. 12, 2018.

(51) Int. Cl.
| | | |
|---|---|---|
| *A61N 1/375* | (2006.01) | |
| *H01R 13/11* | (2006.01) | |
| *A61N 1/36* | (2006.01) | |
| *A61N 1/362* | (2006.01) | |

(52) U.S. Cl.
CPC .......... *A61N 1/3752* (2013.01); *H01R 13/111* (2013.01); *A61N 1/362* (2013.01); *A61N 1/3605* (2013.01); *H01R 2201/12* (2013.01)

(58) Field of Classification Search
CPC  H01R 13/187; H01R 13/111; H01R 13/5224; H01R 2201/12; A61N 1/3752; A61N 1/3605; A61N 1/362
See application file for complete search history.

(56) References Cited

U.S. PATENT DOCUMENTS

| | | | |
|---|---|---|---|
| 4,214,804 A | | 7/1980 | Little |
| 4,245,642 A | | 1/1981 | Skubitz et al. |
| 4,401,359 A | * | 8/1983 | Frelk ..................... H01R 13/20 |
| | | | 439/846 |
| 4,577,643 A | | 3/1986 | Beranek |
| 4,764,132 A | * | 8/1988 | Stutz, Jr. .............. A61N 1/3752 |
| | | | 439/810 |
| 4,898,173 A | | 2/1990 | Daglow et al. |
| 5,261,395 A | | 11/1993 | Oleen et al. |
| 5,413,595 A | | 5/1995 | Stutz, Jr. |

(Continued)

FOREIGN PATENT DOCUMENTS

| | | |
|---|---|---|
| EP | 3 093 927 A1 | 11/2016 |
| GB | 2484578 A | 4/2012 |

(Continued)

*Primary Examiner* — Oscar C Jimenez
(74) *Attorney, Agent, or Firm* — Schwegman Lundberg & Woessner, P.A.

(57) ABSTRACT

An implantable medical device includes a housing; and a header mounted to the housing, the header including a header core including a bore with an electrical contact located within the bore, wherein the electrical contact includes: a first longitudinally extending arm cantilever mounted within the bore; and a second longitudinally extending arm cantilever mounted within the bore.

16 Claims, 5 Drawing Sheets

(56) References Cited

U.S. PATENT DOCUMENTS

| | | |
|---|---|---|
| 5,730,628 A | 3/1998 | Hawkins |
| 7,299,095 B1 | 11/2007 | Barlow et al. |
| 7,682,202 B2 | 3/2010 | Arnholt et al. |
| 7,697,989 B1 | 4/2010 | Lim et al. |
| 8,666,494 B2 | 3/2014 | Schramm et al. |
| 8,731,670 B2 * | 5/2014 | Osypka ............... A61N 1/3752 |
| | | 439/909 |
| 8,761,887 B2 | 6/2014 | Schramm et al. |
| 9,089,686 B2 | 7/2015 | Iwen et al. |
| 9,855,413 B2 | 1/2018 | Vadlamudi et al. |
| 2004/0167582 A1 * | 8/2004 | Tvaska ................. A61N 1/375 |
| | | 607/37 |
| 2011/0270363 A1 | 11/2011 | Schramm et al. |
| 2012/0089203 A1 | 4/2012 | Shaffer |
| 2013/0109248 A1 * | 5/2013 | Rothkopf ............ H01R 13/187 |
| | | 439/786 |
| 2013/0110204 A1 | 5/2013 | Lim et al. |
| 2013/0110205 A1 | 5/2013 | Lim et al. |
| 2014/0017954 A1 * | 1/2014 | Zhang ................... H01R 24/58 |
| | | 439/668 |
| 2014/0067034 A1 | 3/2014 | Iwen et al. |
| 2014/0273654 A1 * | 9/2014 | Tziviskos ............. H01R 13/15 |
| | | 439/668 |
| 2016/0233602 A1 * | 8/2016 | Chen ..................... H01R 13/42 |
| 2017/0143978 A1 | 5/2017 | Barker |
| 2017/0201842 A1 * | 7/2017 | Liu ....................... H01R 24/58 |
| 2017/0354825 A1 | 12/2017 | Dadashian et al. |

FOREIGN PATENT DOCUMENTS

| | | |
|---|---|---|
| WO | WO-2005/081927 A2 | 9/2005 |
| WO | WO-2006/026186 A2 | 3/2006 |

\* cited by examiner

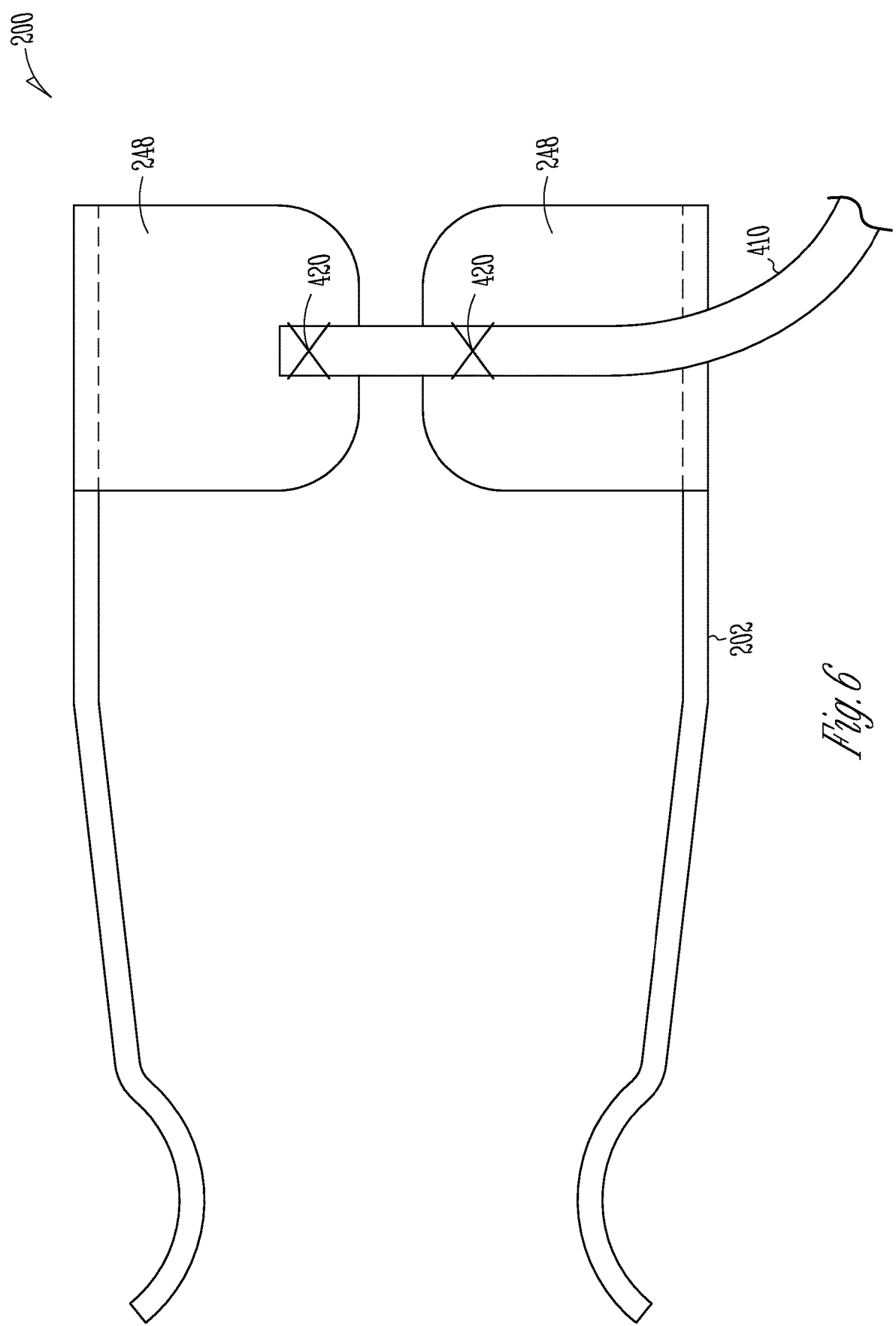

CORE-CLIP PG-LEAD SPRING ELECTRICAL CONTACT

CLAIM OF PRIORITY

This application claims the benefit of priority under 35 U.S.C. § 119(e) of U.S. Provisional Patent Application Ser. No. 62/697,203, filed on Jul. 12, 2018, which is herein incorporated by reference in its entirety.

BACKGROUND

Leads implanted in or about the heart have been used to reverse certain life-threatening arrhythmia, or to stimulate contraction of the heart. Electrical energy is applied to the heart via electrodes on the leads to return the heart to normal rhythm.

A header on an implantable device is used to couple a conductor of the lead with circuitry within the implantable device. For instance, a contact in the header is used to electrically couple a cardiac stimulator system with the lead electrode for making contact with a portion of the heart.

OVERVIEW

Example 1 can include subject matter that can include an implantable medical device including a housing; and a header mounted to the housing, the header including a header core including a bore with an electrical contact located within the bore, wherein the electrical contact includes: a first longitudinally extending arm cantilever mounted within the bore; and a second longitudinally extending arm cantilever mounted within the bore.

In Example 2, the subject matter of Example 1 can optionally include the first longitudinally extending arm and the second longitudinally extending arm each including a first, mounting end positioned within a mounting slot in the header core and a second, free end located within a cavity in the bore.

In Example 3, the subject matter of Example 2 can optionally include the first longitudinally extending arm and the second longitudinally extending arm each including an intermediate section located between the first mounting, end and the second free end, the intermediate section positioned within a widened slot cavity in the core that is wider than the mounting slot.

In Example 4, the subject matter of Example 3 can optionally include the widened slot cavity defining a triangular shaped slot defining a lower surface, with a bottom surface of the intermediate main spring section resting on the lower surface when a lead terminal is not positioned within the bore.

In Example 5, the subject matter of Example 4 can optionally include the triangular shaped slot limiting the inward bias of the first end second longitudinally extending arms.

In Example 6, the subject matter of any of Examples 2-5 can optionally include the first longitudinally extending arm and the second longitudinally extending arm each including a connection section which extends perpendicularly from the mounting end and provides a connection surface to connect to a feedthrough.

In Example 7, the subject matter of Example 6 can optionally include the connection sections of the first longitudinally extending arm and the second longitudinally extending arm being connected together.

In Example 8, the subject matter of any of Examples 1-7 can optionally include the first longitudinally extending arm and the second longitudinally extending arm are each biased towards a center of the bore and deflect in opposite directions from each other when a lead is inserted therebetween.

In Example 9, the subject matter of any of Examples 2-8 can optionally include the first longitudinally extending arm and the second longitudinally extending arm each including a contact portion on the second, free end that curves toward a center of the bore.

In Example 10, the subject matter of Example 9 can optionally include a separate material located on the contact portion.

In Example 11, the subject matter of any of Examples 1-10 can optionally include a cover attached to the header and located over the bore and the electrical contact.

In Example 12, the subject matter of any of Examples 1-11 can optionally include a lead including a terminal configured to be received within the bore.

Example 13 can include subject matter that can include a method including forming an electrical contact including first and second longitudinally extending arms; and placing the electrical contact into a header bore of an implantable device such that each of the first and second arms are cantilevered mounted within the bore.

In Example 14, the subject matter of Example 13 can optionally include the first longitudinally extending arm and the second longitudinally extending arm each including a first, mounting end positioned within a mounting slot in the header core and a second, free end located within a cavity in the bore.

In Example 15, the subject matter of any of Examples 13-14 can optionally include the first longitudinally extending arm and the second longitudinally extending arm each including an intermediate section located between the first mounting, end and the second free end, the intermediate section positioned within a widened slot cavity in the core that is wider than the mounting slot.

Example 16 can include subject matter that can include an implantable medical device including a housing; and a header mounted to the housing, the header including a header core including a bore with an electrical contact located within the bore, wherein the electrical contact includes: a first longitudinally extending arm cantilever mounted within the bore; and a second longitudinally extending arm cantilever mounted within the bore.

In Example 17, the subject matter of Example 16 can optionally include the first longitudinally extending arm and the second longitudinally extending arm each including a first, mounting end positioned within a mounting slot in the header core and a second, free end located within a cavity in the bore.

In Example 18, the subject matter of Example 17 can optionally include the first longitudinally extending arm and the second longitudinally extending arm each including an intermediate section located between the first mounting, end and the second free end, the intermediate section positioned within a widened slot cavity in the core that is wider than the mounting slot.

In Example 19, the subject matter of Example 18 can optionally include the widened slot cavity defining a triangular shaped slot defining a lower surface, with a bottom surface of the intermediate main spring section resting on the lower surface when a lead terminal is not positioned within the bore.

In Example 20, the subject matter of Example 19 can optionally include the triangular shaped slot limiting the inward bias of the first end second longitudinally extending arms.

In Example 21, the subject matter of any of Examples 17-20 can optionally include the first longitudinally extending arm and the second longitudinally extending arm each including a connection section which extends perpendicularly from the mounting end and provides a connection surface to connect to a feedthrough.

In Example 22, the subject matter of Example 21 can optionally include the connection sections of the first longitudinally extending arm and the second longitudinally extending arm being connected together.

In Example 23, the subject matter of any of Examples 16-22 can optionally include the first longitudinally extending arm and the second longitudinally extending arm are each biased towards a center of the bore and deflect in opposite directions from each other when a lead is inserted therebetween.

In Example 24, the subject matter of any of Examples 17-25 can optionally include the first longitudinally extending arm and the second longitudinally extending arm each including a contact portion on the second, free end that curves toward a center of the bore.

In Example 25, the subject matter of Example 24 can optionally include a separate material located on the contact portion.

In Example 26, the subject matter of any of Examples 16-25 can optionally include a cover attached to the header and located over the bore and the electrical contact.

In Example 27, the subject matter of any of Examples 16-26 can optionally include a lead including a terminal configured to be received within the bore.

Example 28 can include subject matter that can include an implantable medical device including a housing; and a header mounted to the housing, the header including a header core having a bore with an electrical contact located within the bore, wherein the header core includes a mounting slot and a widened slot cavity that is wider than the mounting slot and a cavity; wherein the electrical contact includes: a first longitudinally extending arm cantilever mounted within the bore; and a second longitudinally extending arm cantilever mounted within the bore; wherein the first longitudinally extending arm and the second longitudinally extending arm each include a first, mounting end positioned within the mounting slot and a second, free end located within the cavity in the header core and each include an intermediate main spring section located between the first mounting end and the second free end, the intermediate section being positioned with the widened slot cavity, wherein the first longitudinally extending arm and the second longitudinally extending arm each include a connection section which extends perpendicularly from the mounting section and provides a connection surface to connect to a feedthrough.

In Example 29, the subject matter of Example 28 can optionally include the widened slot cavity defining a triangular shaped slot, with a bottom surface of the intermediate main spring section resting thereon when a lead terminal is not positioned within the bore, wherein the triangular shaped slot limits the bias of the first end second longitudinally extending arm In Example 30, the subject matter of any of Examples 28-29 can optionally include the connection sections of the first longitudinally extending arm and the second longitudinally extending arm connected together.

In Example 31, the subject matter of any of Examples 28-30 can optionally include the first longitudinally extending arm and the second longitudinally extending arm are each biased towards a center of the bore and deflect in opposite directions from each other when a lead is inserted therebetween.

In Example 32, the subject matter of any of Examples 28-31 can optionally include the first longitudinally extending arm and the second longitudinally extending arm each including a contact portion on the second, free end that curves toward a center of the bore.

Example 33 can include subject matter that can include a method including forming an electrical contact including first and second longitudinally extending arms; and placing the electrical contact into a header bore of an implantable device such that each of the first and second arms are cantilevered mounted within the bore.

In Example 34, the subject matter of Example 33 can optionally include the first longitudinally extending arm and the second longitudinally extending arm each including a first, mounting end positioned within a mounting slot in the header core and a second, free end located within a cavity in the bore.

In Example 35, the subject matter of any of Examples 33-34 can optionally include the first longitudinally extending arm and the second longitudinally extending arm each including an intermediate section located between the first mounting, end and the second free end, the intermediate section positioned within a widened slot cavity in the core that is wider than the mounting slot.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6 shows a side view of a feedthrough connection to a contact, in accordance with one embodiment.

DETAILED DESCRIPTION

Figure 1:
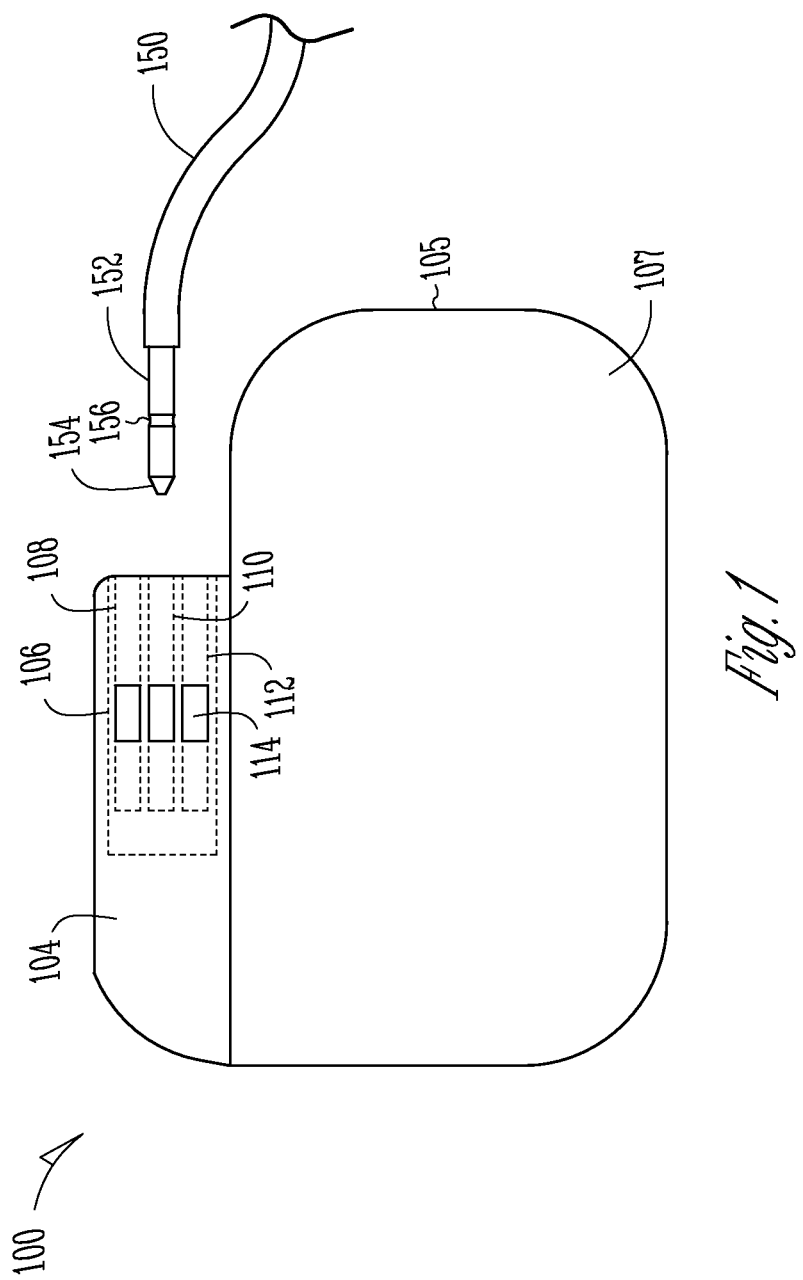
FIG. 1 shows a view of an implantable system according to at least one example.

FIG. 1 shows an implantable system 100, in accordance with one embodiment. The implantable system 100 includes a pulse generator 105 and at least one lead 150. The pulse generator 105 includes a housing 107 and a header 104 mounted to the housing 107. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include a power supply such as a battery, a capacitor, and other components housed in the housing 107. The pulse generator 105 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

In other embodiments, implantable system 100 can also be suitable for use with implantable electrical stimulators, such as, but not limited to, neuro-stimulators, skeletal stimulators, central nervous system stimulators, or stimulators for the treatment of pain.

The lead 150 includes a lead body having a proximal end, where a terminal 152 of the lead 150 can be coupled to the header 104 of the pulse generator 105. The lead 150 extends to a distal end, which can be coupled with a portion of a heart, when implanted. The distal end of the lead 150 includes at least one electrode which electrically couples the lead 150 with the heart. At least one electrical conductor is disposed within the lead 150 and extends from the proximal end to the electrode. The electrical conductor carries electrical currents and signals between the pulse generator 105 and the electrode.

The header 104 includes one or more bores 108, 110, 112 formed within a header core 106 and configured to receive the lead terminal 152 of the lead 150. In this example, the lead terminal 152 includes a proximal tip contact 154, and a ring contact 156. In other examples, the lead terminal 152 can include multiple ring contacts. The terminal contacts 154, 156 can be made of stainless steel while insulative portions of terminal 152 can be formed of polyurethane.

Within the header core 106 each of the one or more bores 108, 110, 112 can including one or more electrical contacts 114 (shown schematically) located within the bores 108, 110, 112. The contacts 114 can be connected to a feedthrough to electrically communicate between the lead 150 and the electronics within the pulse generator housing 107.

One problem of present header electrical contacts, such as leaf and coil spring contacts, is increased impedance. This increased impedance can be caused by inadequate contact force between the lead terminal and the contact within the header. For example, the objective is to have a contact force of about 2 N per contact. However, size constraints within the header limit the ability to achieve the target contact load without yielding the spring while also accommodating the expected range of spring deflection. Moreover, raising contact force can increase the lead insertion force. Accordingly, contact 114 is designed to help alleviate these issues.

Figure 2:
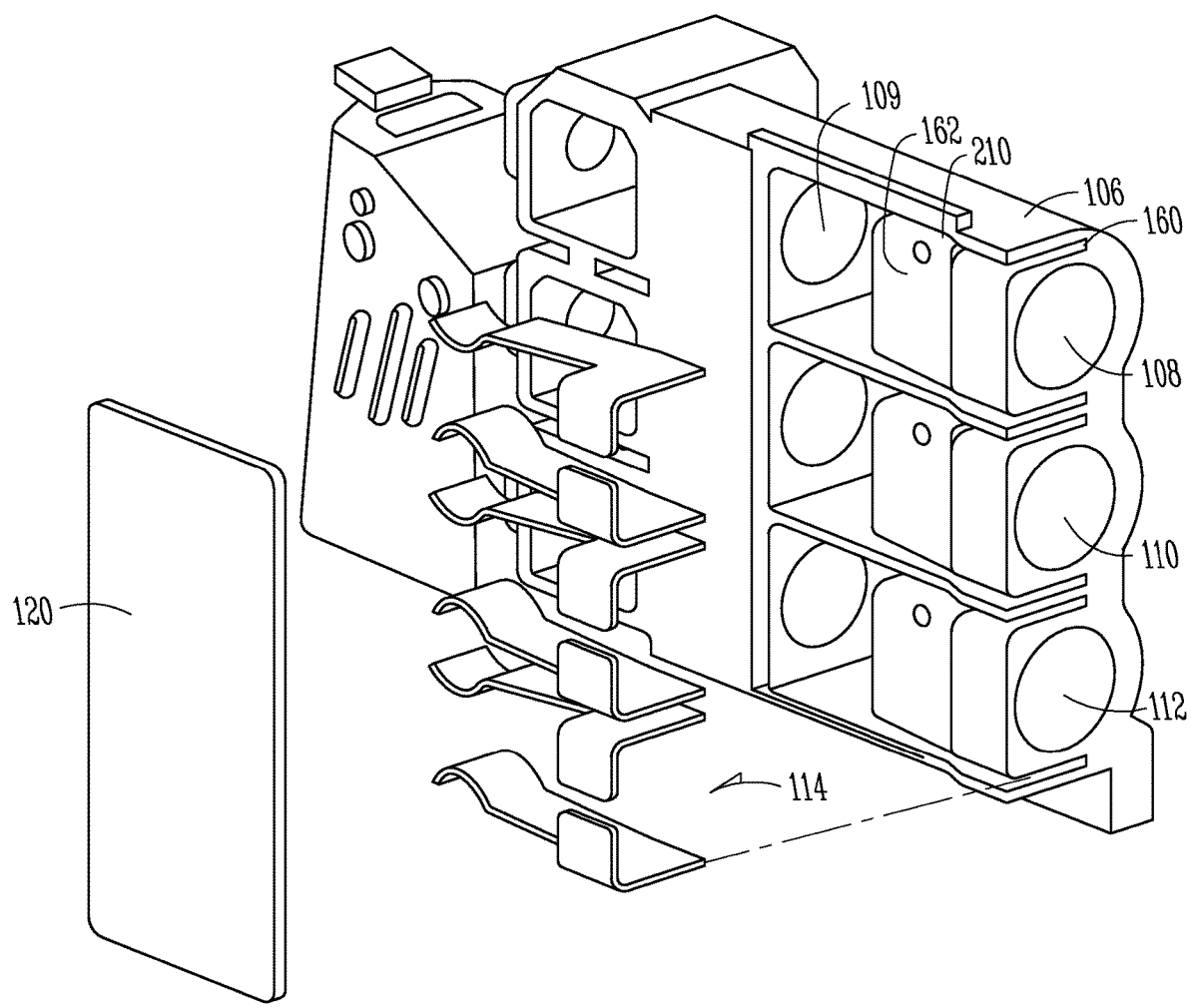
FIG. 2 shows an exploded perspective view of a core block for a header, in accordance with one example.
Figure 3:
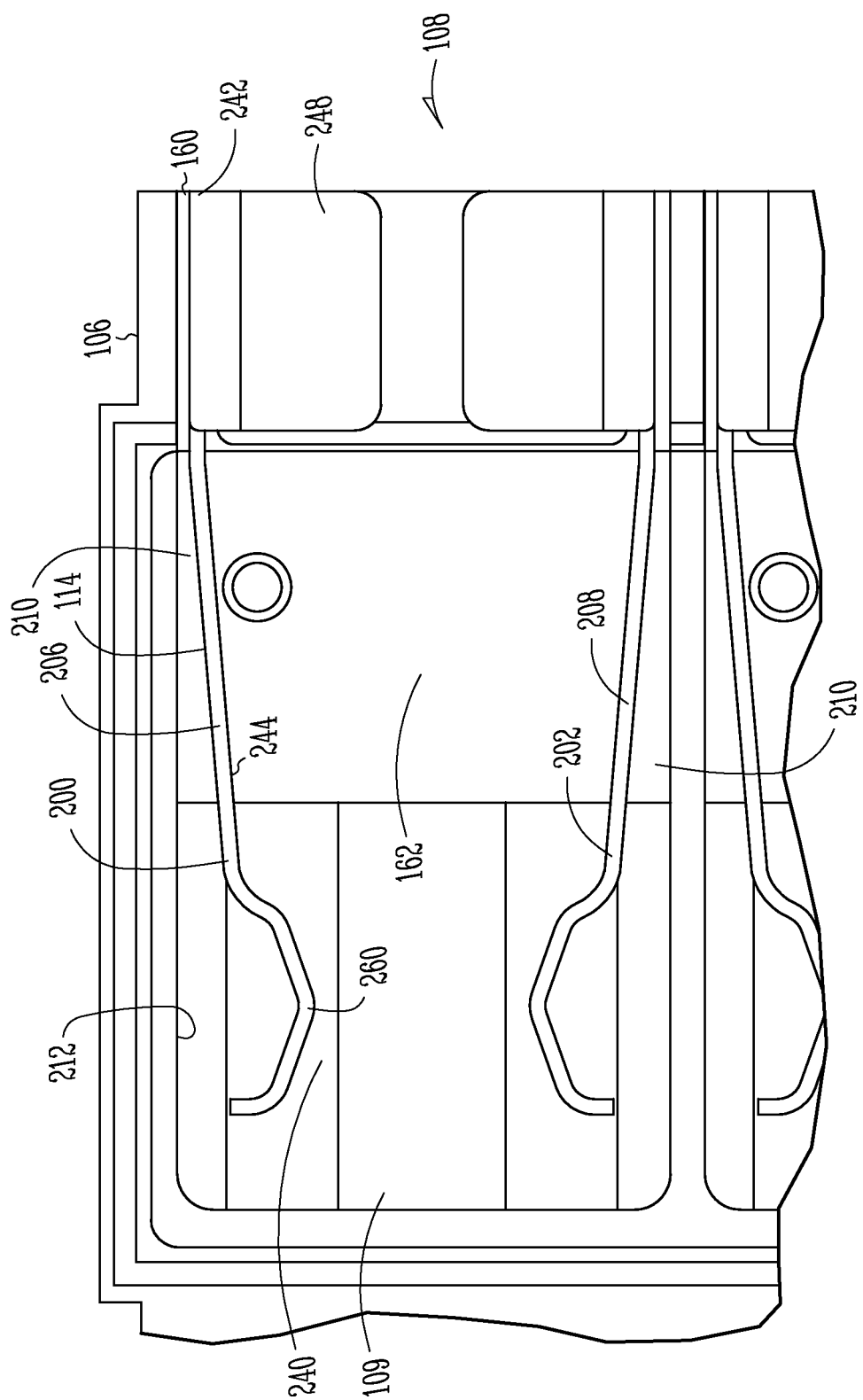
FIG. 3 shows a side view of the core block of FIG. 2, in accordance with one example.
Figure 4:
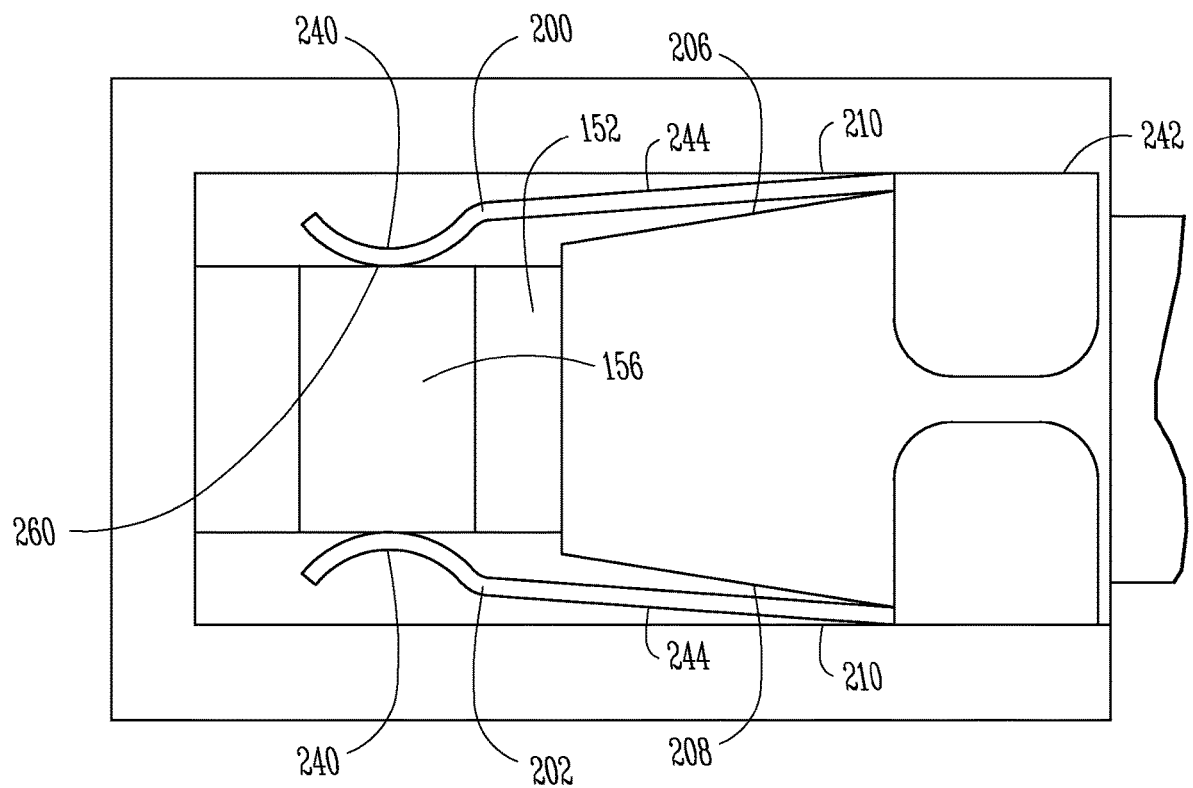
FIG. 4 shows another side view of the core block of FIG. 2.
Figure 5:
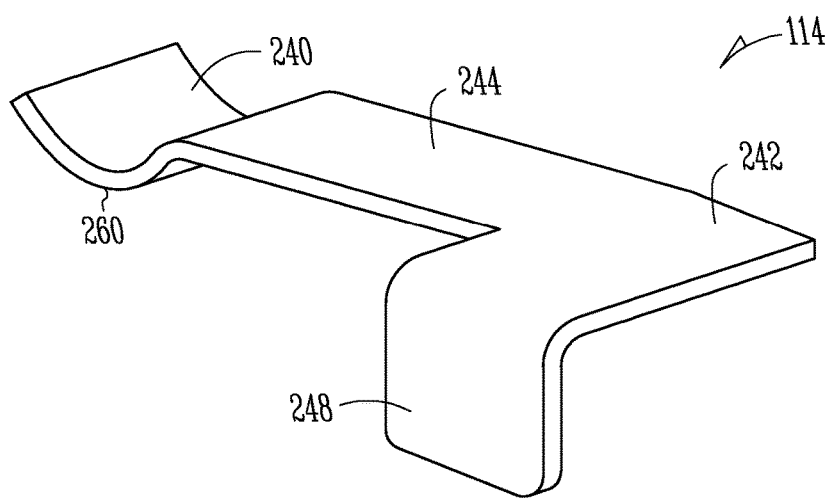
FIG. 5 shows a perspective view of a contact for a header, in accordance with one embodiment.

FIGS. 2, 3, 4, and 5 show certain features of the contact 114, in accordance with one embodiment. FIG. 2 shows an exploded perspective view of the core block 106 for a header with the contacts 114, in accordance with one example. FIG. 3 shows a side view of the core block 106 with the contacts 114 mounted therein. FIG. 4 shows another side view of the core block 106, and FIG. 5 shows a perspective view of an arm of the contact 114.

For ease of description, the following description discusses bore 108, while the discussion applies also to bores 110 and 112. Likewise, although each contact 114 includes a first longitudinally extending arm 200 cantilever mounted within the bore 108 and a second longitudinally extending arm 202 cantilever mounted within the bore 108, the discussion will often discuss only one of the arms 200, 202 with the understanding that the description applies to both.

In this example, the electrical contact between the lead terminal 152 and the header is formed by contacts 114. As noted, each contact 114 includes a first longitudinally extending arm 200 cantilever mounted within the bore 108 and a second longitudinally extending arm 202 cantilever mounted within the bore 108.

The header core 106 can include an injection molded header core and the arms 200, 202 can be formed by metal forming, such as stamping the shape and bending the shape to final form.

The first longitudinally extending arm 200 and the second longitudinally extending arm 202 each include a first, mounting end 242 positioned within a mounting slot 160 in the header core 106 and a second, free end 240 located within a cavity 109 in the bore 108. With this design, the contact 114 is integrated into the header core 106 which eliminates the need for a connector block.

Here, the first longitudinally extending arm 200 and the second longitudinally extending arm 202 each include an intermediate section 244 located between the first mounting, end 242 and the second free end 240, the intermediate section 244 positioned within a widened slot cavity 210 in the core 106 that is wider than the mounting slot 160.

In one example, the widened slot cavity 210 defines a triangular shaped slot defining a lower surface 206 (or an upper surface 208) on a core portion 162. The arms 200, 202 are shaped so as to be biased towards a center of the bore 108 such that a bottom surface of the intermediate main section 244 rests on the lower surface 206 when a lead terminal 152 is not positioned within the bore 108. In one example, the lower and upper surfaces 206, 208 defined by the triangular shaped slots 210 limit the inward bias of the first and second longitudinally extending arms 200, 202.

The first longitudinally extending arm 200 and the second longitudinally extending arm 202 each include a contact portion 260 on the second, free end 240 that curves toward a center of the bore 108. There can be design flexibility in the shape of the lead interfacing part of contact portion 260 of the arm 200. Thus, the contact point and shape of the arm 200 can be shaped to match the lead terminal and increase surface area. In one example, the arms 200, 220 have a length and a width to provide a contact force of 1.5 N to 2.5 N.

In one example, a separate material can be located on the contact portion 260, such as a "slug" of other material at contact portion 260 (e.g. precious metal, porous metal with conductive lubricant, harder material, softer material, conductive polymer).

One or more covers 120 can be attached to the header core 106 and located over the bore and the electrical contact 114. After the connections are made, the entire structure can then be overmolded.

Here, the first longitudinally extending arm 200 and the second longitudinally extending arm 202 each include a connection section 248 which extends perpendicularly from the mounting end 242 and provides a flat connection surface to connect to a feedthrough, as will be further discussed below. Thus, part of the contact 114 sits over the side of the core to provide the spot weld surface for the feedthrough wire connection.

FIG. 3 and FIG. 4 show how the first longitudinally extending arm 200 and the second longitudinally extending arm 202 are each biased towards a center of the bore 108 and deflect in opposite directions from each other when a lead terminal 152 is inserted therebetween.

FIG. 6 shows a side view of a feedthrough connection to a contact, in accordance with one embodiment. Here, the first longitudinally extending arm 200 and the second longitudinally extending arm 202 each include the connection section 248 which extends perpendicularly from the mounting end 242 and provides a connection surface to connect to a feedthrough 410. Given the set of materials available and the constraints on space, the present contact 114 is dependent on having a high allowable tensile yield stress (FTY) in the spring material of the arms 200, 202. However, the tensile yield stress is highly dependent on manufacturing processing, especially cold-working and heat-treatment. Both of these can be degraded by heat exposure. Thus, the present design, by providing connection section 248 away from the bending areas of arms 200, 220 avoids having the high bending stress region of the arms 200, 202 heat-affected by processes such as welding.

In one example, the connection sections 248 of the first longitudinally extending arm 200 and the second longitudinally extending arm 202 are connected together defining a single connection section for the first and second arms 200, 202. Thus, in one embodiment, the arms 200, 202 can be integral to each other.

Among other advantages, the present system can help produce more reliable IS-1 (and other lead type) electrical connections at the ring contact 156 of the lead terminal 152. This system does this by allowing more flexibility in the design, especially length and width of the arms 200, 202. For example, because of this design flexibility, Titanium Gr5 can be used for the spring instead of coldworked MP35 N. Moreover, the system eliminates the typical ring connector block and provides both the lead connection and the spot-weld location for the feedthrough wire connection.

Moreover, the present system makes it more feasible to reliably provide the needed contact load at the ring contact in the PG header. The system can cost less than current connector blocks (unit cost). It allows for use of less expensive materials for the spring contact. This system allows significantly longer and wider springs to be used, when compared to existing connector blocks. This allows for a larger nominal deflection on lead insertion which allows for a relatively constant contact load for the expected range of deflections.

Thus, a large relative length allows for very "flat" performance of contact load, and a low bending stress for a given contact load, while the width can be accommodated, further reducing bending stress.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
  a housing; and
  a header mounted to the housing, the header including a header core including a bore with an electrical contact located within the bore, wherein the electrical contact includes:
    a first longitudinally extending arm cantilever mounted within the bore; and
    a second longitudinally extending arm cantilever mounted within the bore; and
    wherein the first longitudinally extending arm and the second longitudinally extending arm each include a first, mounting end positioned within a mounting slot in the header core and a second, free end located within a cavity in the bore, wherein the first longitudinally extending arm and the second longitudinally extending arm each include an intermediate section located between the first mounting end and the second free end, the intermediate section positioned within a widened slot cavity in the core that is wider than the mounting slot, wherein the widened slot cavity defines a triangular shaped slot defining a lower surface, with a bottom surface of the intermediate main spring section resting on the lower surface when a lead terminal is not positioned within the bore, wherein the triangular shaped slot limits the inward bias of the first end second longitudinally extending arms.

2. The implantable medical device of claim 1, wherein the first longitudinally extending arm and the second longitudinally extending arm each include a connection section which extends perpendicularly from the mounting end and provides a connection surface to connect to a feedthrough.

3. The implantable medical device of claim 2, wherein the connection sections of the first longitudinally extending arm and the second longitudinally extending arm are connected together.

4. The implantable medical device of claim 1, wherein the first longitudinally extending arm and the second longitudinally extending arm are each biased towards a center of the bore and deflect in opposite directions from each other when a lead is inserted therebetween.

5. The implantable medical device of claim 1, wherein the first longitudinally extending arm and the second longitudinally extending arm each include a contact portion on the second, free end that curves toward a center of the bore.

6. The implantable medical device of claim 5, further including a separate material located on the contact portion.

7. The implantable medical device of claim 1, further including a cover attached to the header and located over the bore and the electrical contact.

8. The implantable medical device of claim 1, further including a lead including a terminal configured to be received within the bore.

9. An implantable medical device comprising:
a housing; and
a header mounted to the housing, the header including a header core having a bore with an electrical contact located within the bore, wherein the header core includes a mounting slot and a widened slot cavity that is wider than the mounting slot and a cavity;
wherein the electrical contact includes:
a first longitudinally extending arm cantilever mounted within the bore; and
a second longitudinally extending arm cantilever mounted within the bore;
wherein the first longitudinally extending arm and the second longitudinally extending arm each include a first, mounting end positioned within the mounting slot and a second, free end located within the cavity in the header core and each include an intermediate main spring section located between the first mounting end and the second free end, the intermediate section being positioned with the widened slot cavity, wherein the first longitudinally extending arm and the second longitudinally extending arm each include a flat, planar connection section which extends perpendicularly from the mounting section and is exposed on a side surface of the header core and provides a flat, planar connection surface to connect to a feedthrough.

10. The implantable medical device of claim 9, wherein the widened slot cavity defines a triangular shaped slot, with a bottom surface of the intermediate main spring section resting thereon when a lead terminal is not positioned within the bore, wherein the triangular shaped slot limits the bias of the first end second longitudinally extending arm.

11. The implantable medical device of claim 9, wherein the connection sections of the first longitudinally extending arm and the second longitudinally extending arm are connected together.

12. The implantable medical device of claim 9, wherein the first longitudinally extending arm and the second longitudinally extending arm are each biased towards a center of the bore and deflect in opposite directions from each other when a lead is inserted therebetween.

13. The implantable medical device of claim 9, wherein the first longitudinally extending arm and the second longitudinally extending arm each include a contact portion on the second, free end that curves toward a center of the bore.

14. A method comprising:
forming an electrical contact including first and second longitudinally extending arms; and
placing the electrical contact into a header core of an implantable device such that each of the first and second arms are cantilevered mounted within a bore
wherein the first longitudinally extending arm and the second longitudinally extending arm each include a first, mounting end positioned within a mounting slot in the header core and a second, free end located within a cavity in the bore, wherein the first longitudinally extending arm and the second longitudinally extending arm each include an intermediate section located between the first mounting, end and the second free end, the intermediate section positioned within a widened slot cavity in the core that is wider than the mounting slot, wherein the widened slot cavity defines a triangular shaped slot defining a lower surface, with a bottom surface of the intermediate main spring section resting on the lower surface when a lead terminal is not positioned within the bore, and wherein the triangular shaped slot limits the inward bias of the first end second longitudinally extending arms.

15. The method of claim 14, wherein the first longitudinally extending arm and the second longitudinally extending arm each include a connection section which extends perpendicularly from the mounting end and provides a connection surface to connect to a feedthrough.

16. The method of claim 15, wherein the first longitudinally extending arm and the second longitudinally extending arm each include a flat, planar connection section which extends perpendicularly from the mounting section and is exposed on a side surface of the header core and provides a flat, planar connection surface to connect to a feedthrough.

* * * * *